United States Patent
Chen

(10) Patent No.: US 9,504,279 B2
(45) Date of Patent: Nov. 29, 2016

(54) AUTOMIZATION NOZZLE OF ELECTRONIC ATOMIZATION INHALER

(75) Inventor: Zhiping Chen, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 417 days.

(21) Appl. No.: 13/824,335

(22) PCT Filed: Mar. 19, 2012

(86) PCT No.: PCT/CN2012/000347
§ 371 (c)(1),
(2), (4) Date: Sep. 21, 2013

(87) PCT Pub. No.: WO2012/152053
PCT Pub. Date: Nov. 15, 2012

(65) Prior Publication Data
US 2014/0007863 A1    Jan. 9, 2014

(30) Foreign Application Priority Data
May 12, 2011  (CN) .......................... 2011 1 0125093

(51) Int. Cl.
*A61M 11/00* (2006.01)
*A24F 47/00* (2006.01)
*H05B 3/80* (2006.01)

(52) U.S. Cl.
CPC ............. *A24F 47/008* (2013.01); *A61M 11/00* (2013.01); *H05B 3/80* (2013.01)

(58) Field of Classification Search
None
See application file for complete search history.

(56) References Cited

U.S. PATENT DOCUMENTS

| | | | | |
|---|---|---|---|---|
| 5,054,477 A * | 10/1991 | Terada | .................. | A61M 11/06 128/200.14 |
| 6,095,153 A * | 8/2000 | Kessler | ................. | A24F 47/008 131/194 |
| 7,726,320 B2 * | 6/2010 | Robinson | .............. | A24F 47/008 131/194 |
| 7,997,280 B2 * | 8/2011 | Rosenthal | ............ | A61M 11/041 128/202.21 |
| 8,915,254 B2 * | 12/2014 | Monsees | ............... | A24F 47/006 131/194 |
| 2005/0016550 A1 * | 1/2005 | Katase | .................. | A24F 47/002 131/194 |
| 2009/0272379 A1 * | 11/2009 | Thorens | ................... | A24D 3/18 128/202.21 |
| 2011/0011396 A1 * | 1/2011 | Fang | .................... | A24F 47/008 128/202.21 |
| 2011/0094523 A1 * | 4/2011 | Thorens | ................ | A24F 47/008 131/194 |
| 2011/0277757 A1 * | 11/2011 | Terry | .................... | A24F 47/008 128/202.21 |
| 2011/0277764 A1 * | 11/2011 | Terry | .................... | A24F 47/008 128/203.26 |

* cited by examiner

*Primary Examiner* — Bradley Philips
*Assistant Examiner* — Eric Bryant
(74) *Attorney, Agent, or Firm* — Polsinelli PC

(57) ABSTRACT

An atomizing nozzle of an electronic atomizing inhalator is provided. The inhalator includes a casing body, a closure wall at the opening of the front end of the casing body, a gas-outlet aperture on the closure wall, and a rear closure provided at the opening of the rear end of the casing body. A gas-inlet aperture is in the rear closure. A liquid-container and heater are provided in the cavity formed by the casing body, the closure wall and the rear closure. An airflow-passage connecting to the gas-outlet aperture is provided between the casing body and the liquid-container. A liquid-guiding device closes the liquid-container at the opening of the liquid-container. No liquid-storage medium is provided in the liquid-container. A connection-passage for connecting the airflow-passage and the gas-inlet aperture is provided between the liquid-guiding device and the rear closure. The heater is provided on the top of the rear closure, contacting the lower surface of the liquid-guiding device, with at least part of the heater located in the connection-passage.

12 Claims, 3 Drawing Sheets

AUTOMIZATION NOZZLE OF ELECTRONIC ATOMIZATION INHALER

FIELD OF THE INVENTION

Figure 1:
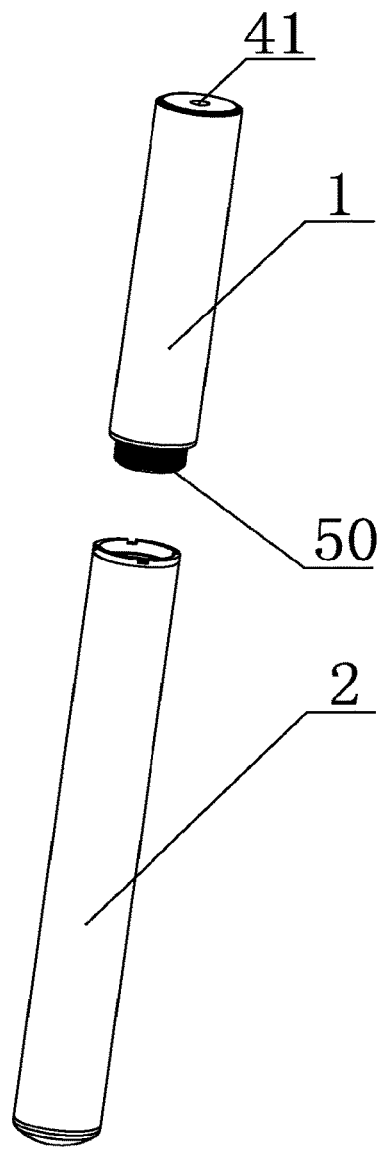

The present invention relates to an electrical atomizing apparatus which is used for atomizing an aromatic liquid for a user to inhale, and especially relates to the development of a structure for the atomizing nozzle of the electrical atomizing apparatus.

BACKGROUND OF THE INVENTION

Electrical atomizers of the inhalation style are normally used to simulate smoker's goods or as an inhalator for the inhalation of medicaments for treating respiratory diseases. The atomizer comprises a cylindrical part containing a power supply and control system, a liquid-atomizing part connected to the cylindrical part, and a suction nozzle. According to the prior art, the liquid-atomizing part and the suction nozzle can be incorporated to be one assembly, alternatively, the liquid atomizing part and the suction nozzle also can be arranged separately and are connected to each other by inserting or bonding.

A typical structure of the prior art is disclosed in Chinese patent ZL200420031182.0 entitled "Atomizing electrical cigarette", including a casing body 14 and a suction nozzle 15, an inlet port 4 provided on the outer wall of the casing body 14, an electronic circuit board 3, an ordinary pressure chamber 5, a sensor 6, a gas-liquid separator 7, an atomizer 9 and a liquid-supplying bottle 11 are successively mounted in the casing body 14; a multi-apertured part 28 for containing liquid is provided in the liquid-supplying bottle 11; The atomizer 9 is held in contact with the supplying bottle 11 by a formation 36, an atomizing chamber 10 is provided in the atomizer 9; a shielding ring 13 for locking the liquid-supplying bottle 11 is provided between one side of the liquid-supplying bottle 11 and the casing body 14. A gas passage 12 is provided on another side of the liquid-supplying bottle 11. An inlet port 4, an ordinary pressure chamber 5, a gas-liquid separator 7, an atomizer 9, a gas passage 12, an air-draining port 17 and a suction nozzle 15 are connected orderly. Although on the base of the prior art, which utilises ultrasound and mechanical atomizing technology, there is already a big improvement with a structure for an electronics cigarette product, such as making use of capillarity action of the liquid for the atomizer 9, adopting a ceramic for the atomizing chamber 10, inhaling the liquid from the liquid-supplying bottle 11 using foamed metal, so as to atomize the liquid in the atomizing chamber 10 at high temperature, and arranging a gas-liquid separator 7 on the gas passage 12. Whilst the product described above usually has a complicated structure and a high manufacturing cost, it is difficult to assemble the main parts of the product and additionally, the multi-apertured part 28 provided in the liquid-supplying bottle 11 also leads to the decrease of the liquid volume contained in the liquid-supplying bottle 11.

Another typical structure of the prior art is disclosed in Chinese patent ZL200720057873.1 entitled "Non-ignitable atomizing electrical cigarette", successively including a controller and generator, a cover with indicator lamp, power equipment, an integral circuit board, a mini gas-transmission switch and a connecting conductor are successively provided in the controller, a connecting conductor, a secondary pressure-maintaining chamber, a liquid-resisting flat, a secondary liquid-storage chamber, a heating apparatus, a liquid-draining mechanism, a liquid-storage chamber and a suction nozzle are successively provided in said generator. There is gas-inlet port provided on one side of the connecting conductor of the generator, the through-aperture is provided between said controller and the connecting conductor of the generator. Although there is already development with the structure of atomizer on the base of the prior art, whilst just like the technical proposal disclosed in ZL200420031182.0, the heating wire is provided in the liquid-draining mechanism, for which it is necessary for the liquid-draining mechanism to be made of hard material, however it is easy to collapse in assembling. Then it is difficult to get a good sealing effect because the liquid is transmitted from the liquid-draining mechanism to the secondary liquid-storage chamber. In addition, the liquid volume possibility to be stored in the storage chamber is reduced because of the storage chamber being made of medicinal cotton fibre.

Another kind of typical structure of the prior art is disclosed in Chinese patent ZL200820124683.1 entitled "Disposable Integrated Electric Atomizing Inhalator", including a rod body, successively comprising the following parts inside: a terminal, which is incorporated with the interior wall, so as to connect to an electric smoking pipe; a terminal core provided on said terminal for electric connection with the electrode of said electric smoking pipe, an atomizer, which is electrically connected with said terminal core, having a gas-vent aperture provided in the atomizer, which is used for atomizing by heating when it is electrified; an insert part of electric atomizing inhalator, which is provided on the top of said atomizer, with liquid-storage medium inside for absorbing or storing the liquid, which is going to be atomized; a top cover of electric atomizing inhalator, which is inserted into the upper end of said rod body, with a gas-passing aperture on it for sealing and preventing the back-flow of said tobacco liquid.

Neither the path for the tobacco liquid being transmitted to the gas-passing aperture nor the process of how the heating apparatus atomizes the tobacco liquid is disclosed in the description of the electric atomizing inhalator mentioned above. In addition, according to the Figures, it is known that one end of said insert part of the electric atomizing inhalator is totally in the structure of wide opening, which is to say that the volume of the tobacco liquid in the insert part of the electric atomizing inhalator is totally depending on the absorbing of the liquid-storage medium, which leads to less of the volume of the tobacco liquid being absorbed by the liquid-storage medium, and once the medium has absorbed a little more of the liquid, it is easy to form a liquid-drop and then the liquid-drop will drop on the frame of said atomizer 5 and deposit on the bottom of the atomizer 5, the tobacco liquid will be charred eventually when the atomizer 5 having heat-storage function and soaking function, and it is difficult for the tobacco liquid deposited on the bottom of the atomizer 5 to be drained out from the gas passage.

SUMMARY OF THE INVENTION

Under the current situation of the relatively developed and stable electric controlling technology, it is especially important to develop the structure of the atomizing nozzle for the electronic atomizing product, in order to obtain a better electronic atomizing product which has a simple structure, and is easy to assemble and convenient and safe to use. One of the main problems trying to be resolved by the present invention is to increase the volume of the liquid being atomized as much as possible, in order to allow people to inhale easily and also to make it easy to assemble and store and safe to use with simple structure. Thereof, based on the prior-art, the following proposal is submitted:

An atomizing nozzle of an electronic atomizing inhalator, comprising a tubular casing body, provided with a closure wall at the opening of the front end of said casing body, with a gas-outlet aperture on said closure wall; and a rear closure provided at the opening of the rear end of said casing body, with a gas-inlet aperture on said rear closure; a liquid-container and heater being provided in the cavity formed by said casing body, said closure wall and said rear closure; an airflow-passage connecting to the gas-outlet aperture is provided between said casing body and said liquid-container; characterized in that the nozzle further comprises a liquid-guiding device, which closes said liquid-container at the opening of said liquid-container, no liquid-storage medium being arranged in the liquid-container; the connection-passage for connecting the airflow-passage and said gas-inlet aperture is provided between said liquid-guiding device and said rear closure, said heater is provided on the top of said rear closure, contacting the lower surface of said liquid-guiding device, with at least part of said heater located in said connection-passage.

Said electronic atomizer is a kind of product used to atomize the liquid contained inside for a consumer to inhale the atomized gas, which at least comprises an atomizing nozzle part and a controlling power part; which are connected by a screw electrode; in which, said controlling power part applies the electric power for the heater in said atomizing nozzle; said heater being used to atomize the liquid in said atomizing nozzle for the consumer to inhale. The liquid-container and heater are provided in said atomizing nozzle. Said atomizing nozzle can be manufactured and assembled as independent parts because the liquid-container, liquid-guiding device and the heater are provided in a cavity, which is formed by the casing body, closure wall and the rear closure. The atomizing nozzle can be used as a disposable part in use, which is to say that when there is no liquid left in said atomizing nozzle, said atomizing nozzle can be replaced conveniently and safely. The consumer inhales the atomized gas in said atomizing nozzle from said closure wall.

The closure wall provided at the opening of the front end of said casing body can be either just a wall plugging the opening of the front end of said casing body, by or a cap-shaped cover covering and closing the opening of the front end of said casing body by way of insertion, screwing or bonding; The gas-outlet aperture provided on said closure wall is used for the convenient outflow of the atomized gas, so that the consumer can inhale the atomized gas in said atomizing nozzle via said gas-outlet aperture.

Said rear closure at first should be a part which can plug the opening of the rear end of said casing body, so as to form the cavity together with said casing body and said closure wall; then, the said rear closure is also used for supporting said heater against the lower surface of said liquid-guiding device. The liquid-guiding device is supported by the upper end of said rear closure to prevent the liquid-guiding device falling from the opening of said liquid-container. A sealing ring can be provided between the back end of said rear closure and the inside of said casing body, so as to prevent the liquid dropping on the rear closure flowing out of said casing body, in addition, it is very convenient to assemble the rear-closure and said casing body by insertion when the sealing ring has been provided, especially when there is a problem of thermal expansion and contraction of the casing body, said sealing ring can automatically adapt to the different space between the rear closure and said casing body, so as to achieve a good sealing effect.

For the convenience of manufacture, said rear closure can be separated into two parts, namely a fixing seat for a heater and a sealing seat, which can be manufactured separately. Said heater and said gas-inlet aperture can be provided on said fixing seat for said heater, said sealing ring is provided between said sealing seat and said casing body, so as to fix them together. Said fixing seat for said heater is supported by said sealing seat, hence said fixing seat for said heater can be made of a heat-resistant material such as ceramics, silicon rubber and the like, whilst said sealing seat can be made of normal metals or non-metallic materials, so as to give full scope to the heating-resistant characteristic of said fixing seat for heater, and the connecting characteristic of said sealing seat, and to simplify the structure of the manufacturing mould itself. In addition, because said fixing seat for heater contacts said heater directly, part of the heat from said heater can be stored by said fixing seat for heater, which can be used to keep the air in said connection-passage and some liquid in said liquid-guiding device above said connection-passage under high temperature, which is good for atomizing the liquid drops in said connection-passage and also good for the permeation of the liquid in said liquid-guiding device to be atomized.

Said liquid-container has a bottle-shaped body with a containing cavity, having a mouth part, from which the liquid in said liquid-container flows out; Liquid can be filled into said liquid-container before use or assembly. Said liquid-container can be manufactured either integral with said casing body, or separately. The shaguipe of the mouth part of said liquid-container can be either of the necked type or open type.

When the shape of the mouth part of said liquid-container is of the necked type, the upper end of said liquid-container can be inserted into said liquid-guiding device directly, or when the liquid-container is dismountable, the upper end of said liquid-container can pass through a spacer at first and then be inserted into said liquid-guiding device. Of course it is also a possibility for the total of or just part of said liquid-guiding device to be inserted into the mouth of said liquid-container, anyway, the liquid in said liquid-container should permeate out slowly.

When the shape of the mouth part of said liquid-container is of the open type, a position step can be provided at the inside of the mouth part of said liquid-container. The mouth part of said liquid-container can be plugged in advance by the spacer provided on said position step. There are liquid-draining apertures on said spacer, and the liquid-guiding device is located under said spacer, the co-operation of said spacer and said liquid-guiding device thus plug the mouth part of said liquid-container, the liquid in said liquid-container then permeating out to said liquid-guiding device through said liquid-draining apertures. In addition, said spacer can either limit the assembled depth of said liquid-guiding device, so as to prevent said liquid-guiding device from being inserted too far into said liquid-container in assembly, or to prevent said liquid-guiding device moving too far towards said liquid-container when said rear closure is supported against said liquid-guiding device.

The mouth part of said liquid-container is plugged by said liquid-guiding device is to say that said liquid-guiding device is provided just at the inside of the mouth part of said liquid-container or just right at the opening of the mouth part of said liquid-container, from which the liquid-guiding device can either prevent the liquid draining directly out from the mouth part of said liquid-container, and also can absorb the liquid in said liquid-container. The liquid in said liquid-container which is going to be atomized then continuously enters into said liquid-guiding device by way of permeation. Because said liquid-guiding is provided just at the inside of the mouth part of said liquid-container or just right at the opening of the mouth part of said liquid-container, and is not provided in the space of said liquid-container for storage liquid, that is also to say there is no medium in said liquid-container for storing liquid. In order to avoid an insufficient seal or a gap between said liquid-guiding device and the mouth part of said liquid-container, it is preferred to insert at least part of said liquid-guiding device directly into the inside of the mouth part of said liquid-container. Said liquid-guiding device can be made of resilient materials, such as cellucotton or sponge or the like, having heat-resistant, non-toxic and multi-apertured characteristics.

In order to make the permeating of the liquid in said liquid-container easier, the further preferred proposal is to arrange a gas pipe in said liquid-container, with one end of said gas pipe inserted in said liquid-guiding device, and another end of said gas pipe extending to the upper part of said liquid-container, the air from the outside of said liquid-container thus penetrates slowly into said liquid-container along said gas pipe so as to avoid an excessive negative pressure in said liquid-container. It is preferred that one end of said gas pipe does not penetrate through said liquid-guiding device, so as to achieve the semi-sealing for said gas pipe by making use of part of the wall of said liquid-guiding device, whilst the air permeates slowly into said gas pipe.

Said connection-passage is the passage for airflow, which is provided between said liquid-guiding device and said rear closure. The air from outside passes through said atomizing nozzle, and then passes through said connection-passage, and then enters into said airflow-passage between said casing body and said liquid-container, thus the heated and atomized liquid flows along said airflow-passage.

There are many kinds of method of forming said connection-passage, one of them is to arrange a depressed cavity at the centre of the top end of said rear closure (or said fixing seat for the heater), with said air-inlet port connected to said depressed cavity, said heater being arranged across the side-wall around said depressed cavity, through-apertures are provided on the side-wall of said depressed cavity. Hence, the side-wall around the upper end of said depressed cavity then supports the heater against said liquid-guiding device and also under said liquid-guiding device, the depressed cavity thus can be thought of as the said connection-passage (as well as the atomizing cavity), the atomized liquid (gas) then passes through the through-apertures on the side-wall of said depressed cavity and enters into said airflow-passage between said casing body and said liquid-container. Another equivalent method of forming said connection-passage is to arrange convex columns on the upper end of said rear closure (or said fixing seat for the heater), the heater is located across said convex columns. The space surrounding said convex columns then forms said connection-passage (namely the atomizing cavity). Secondly, the method also can be of course a combination of the two methods mentioned above. Said connection-passage thus can be naturally formed by the incorporation of the side-wall of said depressed cavity or said convex columns with said liquid-guiding device; once said rear closure (or said fixing seat for the heater) has been assembled to support against said liquid-guiding device, the problem, such as said connection-passage becoming deformed or blocked, can be thus avoided, and also it is ensured that said heater is located in said connection-passage and also against said liquid-guiding device.

Said heater is a part used for heating and atomizing liquid which is positioned on the upper end of said rear closure, so as to contact said liquid-guiding device as much as possible, so that the heater can absorb the liquid on said liquid-guiding device; Secondly, because at least part of said heater is positioned in said connection-passage, the liquid-drops spreading in said connection-passage and on said heater can be atomized by using said heater and can be taken away by the flowing air out to said airflow-passage between said casing body and said liquid-container. The said heater can be made to bend to heat-resisting fibre core, which can make the spreading of the liquid on said liquid-guiding device easier, further, by using of the wick of said heat-resisting fibre core connecting or being near to said liquid-guiding device, liquid drops spreading from said liquid-guiding device and said heater can be absorbed, more liquid drops can be then heated and atomized by said heater. Alternatively, a spreading spacer can be placed at the lower surface of said liquid-guiding device, with said heater contacting the lower surface of said spreading spacer, from which the liquid in said liquid-guiding device can be spread evenly by using said spreading spacer. Said spreading spacer is a kind of flat material, with a better spreading characteristic, whilst not necessarily having a better liquid-storing characteristic than said liquid-guiding device. The spreading spacer can be stuck to the lower surface of said liquid-guiding device. The electrode leg wire of said heater extends through said rear closure and connects to an external power source.

At least part of said heater is located in said connection-passage across the upper end of said rear closure and also contacts the lower surface of said liquid-guiding device or said spreading spacer, and hence it is impossible for the external surface of said heater to be totally exposed in said connection-passage.

For the convenience of assembly and using said heater, the preferred technical proposal is to arrange a semicircular-shaped groove, which should match said heater, on the upper end of said rear closure, said heater should be erected in said semicircular-shaped groove. Hence, under the abutment by the upper end of said rear closure, good contact can be achieved between said heater and the lower surface of said liquid-guiding device or said spreading spacer, whilst ensures that said heater located in said connection-passage.

According to the technical proposal disclosed above, said liquid-container is filled with liquid medium which is going to be atomized, said liquid-container is located in said casing body, then said liquid-guiding device plugs the mouth part of said liquid-container, further, said rear closure provided with said heater is fixed at the opening of the rear end of said casing body, with the upper end of said rear closure (or fixing seat for said heater) abutting against the lower surface of said liquid-guiding device, so that said connection-passage to be formed between the upper end of said rear closure (or fixing seat for said heater) and said liquid-guiding device. Thus, the liquid in said liquid-container spreads to said connection-passage by said liquid-guiding device or the spreading spacer placed at the lower surface of said liquid-guiding device. The flowing air will take the atomized gas out when the heater heats.

The proposal described above is simple in structure and easy to assemble with a good sealing effect, in addition, there are still the following main beneficial effects:

1) because said heater is located on the upper end of said rear closure, and contacts the lower surface of said liquid-guiding device or said spreading spacer provided under said liquid-guiding device, it is easy for the heater itself or the fibre core inside said heater to absorb liquid just by using of the wicking ability and gravity action of the liquid itself.

2) because no medium provided in said liquid-container for storing liquid, the quantity of the liquid able to be stored in every atomizing nozzle of the electronic atomizing inhalator is substantially increased for the same volume of liquid-container, which leads to a durable use and also have resolved the defects of the traditional products, in which a medium has to be used for storing liquid.

3) because said liquid-container is plugged at its mouth part by said liquid-guiding device, the sealing and the draining out for the liquid in said liquid-container can be achieved by making use of the principle of negative pressure and the adhesive characteristic of the liquid itself.

4) because the convex columns are provided on the upper end of said rear closure (or said fixing seat for the heater) and the heater is erected on said convex columns, said connection-passage thus is formed in the space around said convex columns, when said rear closure (or said fixing seat for the heater) has been assembled to abut against said liquid-guiding device, the problem of said connection-passage becoming deformed or blocked up can be avoided, and also ensures that said heater is located in said connection-passage.

Because of such advantages and characteristics mentioned above, the present invention can be applied to the product of an electronic atomizing inhalator.

BRIEF DESCRIPTION OF THE DRAWINGS

Embodiments of the atomizing nozzle of the electronic atomizing inhalator of the present invention will now be described with reference to the accompanying drawings, in which:

FIG. 1 is a schematic illustration of the assembly of the atomizing nozzle of an electronic atomizing inhalator of the present invention with the power supply;

FIG. 2 is an exploded schematic illustration of the atomizing nozzle of the electronic atomizing inhalator of the present invention;

FIG. 3 is a sectional view along the line A-A of FIG. 2;

FIG. 4 is a sectional schematic illustration of the atomizing nozzle of the electronic atomizing inhalator of the present invention; and FIG. 5 is a schematic illustration having a gas pipe on the base of the proposal shown in FIG. 2 and FIG. 4, whilst the shape of the mouth part of said liquid-container is of the necked type.

DETAILED DESCRIPTION OF THE INVENTION

As shown in FIG. 1 of the drawings, the electronic atomizing inhalator is a kind of product for atomizing a liquid contained therein, so as to allow the consumer to inhale the atomized gas therefrom. The inhalator comprises a cylindrical atomizing nozzle 1 and cylindrical control and power portion 2, which are electrically and mechanically connected to each other by a screw-threaded electrode 50. The control and power portion 2 includes a power supply and control circuit etc. The control and power portion 2 is arranged to apply electric power to the atomizing nozzle 1 and is detachably connected to the atomizing nozzle 1 by the screw-threaded electrode 50.

As shown in FIGS. 2 to 4 of the drawings, the atomizing nozzle 1 of the electronic atomizing inhalator comprises a tubular casing body 3.

A closure wall 4 is provided at the open of the front end of the casing body 3, a gas-outlet aperture 41 being provided on it. The closure wall 4, like a cap, engages the wall of the opening at the front end of the casing body 3, the gas-outlet aperture 41 conveniently permits the outflow of atomized gas, so that the consumer can inhale the atomized gas in the atomizing nozzle 1 through the gas-outlet aperture 41.

A rear closure 5 is provided at the open of the rear end of the casing 3, a gas-inlet aperture 51 being provided in the rear closure 5. The rear closure 5 comprises two parts, which are a fixing seat for heater 52 and a sealing seat 53, the gas-inlet aperture 51 being provided on the fixing seat for heater 52. There is also a bigger central aperture 530 provided on the horizontal board part of the sealing seat 53, the central aperture 530 effectively forming the gas-inlet passage of the gas-inlet aperture 51.

Two convex columns 521 are provided on the upper end of the fixing seat for heater 52, with semicircular-shaped grooves 522 being provided on the top end of the convex columns 521. A heater 7 is mounted between the two convex columns 521 and is located in the grooves 522. The two electrode leg wires 70 of the heater 7 pass through the fixing seat for heater 52 and then electrically connect to the controlling power part 2 by the screw electrode 50, in which the connecting screw thread is provided on the outside of the lower end of the sealing seat 53, thereby forming one pole of the screw electrode 50. Another pole of the screw electrode 50 is not shown in the Figures. The hollow tubular sealing seat 53 is fixed from its outside to the opening at the rear end of the casing 3 by sealing ring 8. A step is provided in the cavity of the sealing seat 53, with the central aperture 530 being at the centre of the step, from which the fixing seat for heater 52 thus can be fixed in the upper part of the cavity of the sealing seat 53 by making use of the step. The fixing seat for heater 52 has elasticity because it is made from a heat-resisting silicon rubber, which provides a good sealing effect between the fixing seat for heater 52 and the wall of the cavity of the sealing seat 53, and also provides a certain elasticity when the fixing seat for heater 52 abuts against the lower surface of the liquid-guiding device 9, so as to make the heater 7 more adjacent to the lower surface of a liquid-guiding device 9.

As shown in FIGS. 2 to 4 of the drawings, there is also a liquid-container 6 provided in the cavity formed by the casing body 3, closure wall 4 and rear closure 5. The heater 7 and the liquid-guiding device 9 are arranged between the rear closure 5 and the liquid-container 6.

The liquid-container 6 comprises a bottle-shaped body having a container cavity, which has a wide mouth part, the inside diameter of the mouth part being at least equal to the inside diameter of the cavity of the liquid-container 6. No medium for storing liquid is provided in the liquid-container 6. The liquid 60 to be atomized can be introduced into the liquid-container 6 before the product is used or assembled. The liquid-container 6 and the casing body 3 can be manufactured separately, so as to reduce the difficulty of making moulds.

The liquid-guiding device 9 is a kind of part for preventing the liquid 60 draining directly out from the mouth part of the liquid-container 6. Particularly, the liquid-guiding device 9 can absorb the liquid 60 stored in the liquid-container 6 by way of continuous permeation.

Figure 5:
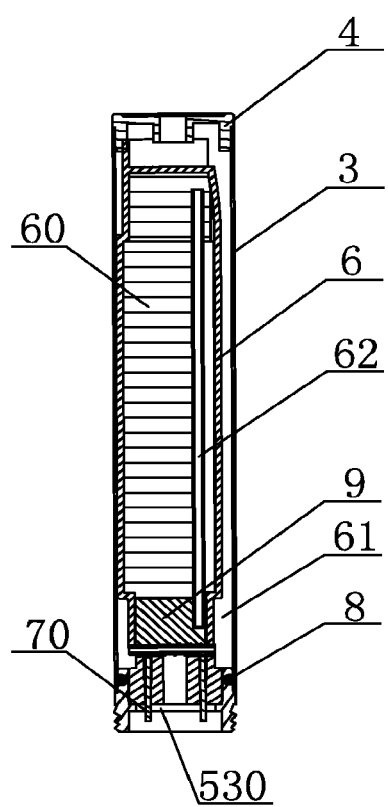

As shown in FIG. 5, in order to make the liquid 60 in the liquid-container 6 permeate more easily, the preferred proposal is to arrange a gas pipe 62 in the liquid-container 6, with one end of the gas pipe 62 inserted in the liquid-guiding device 9, while not penetrating through the wall of the liquid-guiding device 9, and another end of the gas pipe 62 extending to the upper part of the liquid-container 6, which allows the air from the outside of the liquid-container 6 to flow slowly into the liquid-container 6 along the gas pipe 62, so as to avoid an excessive negative pressure in the liquid-container 6. The liquid-guiding device can be made from cellucotton or sponge, which should be a heat-resisting, non-toxic and multi-apertured material.

Figure 2:
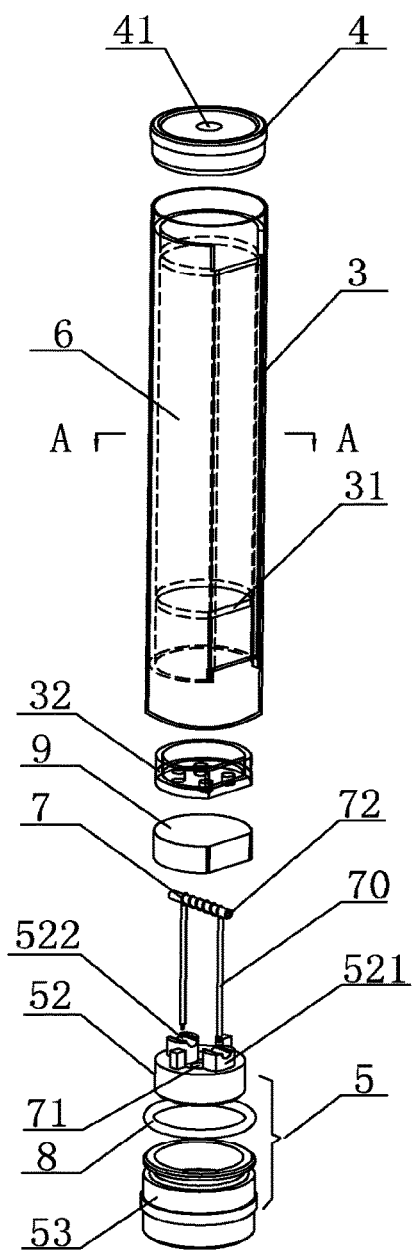
Figure 4:
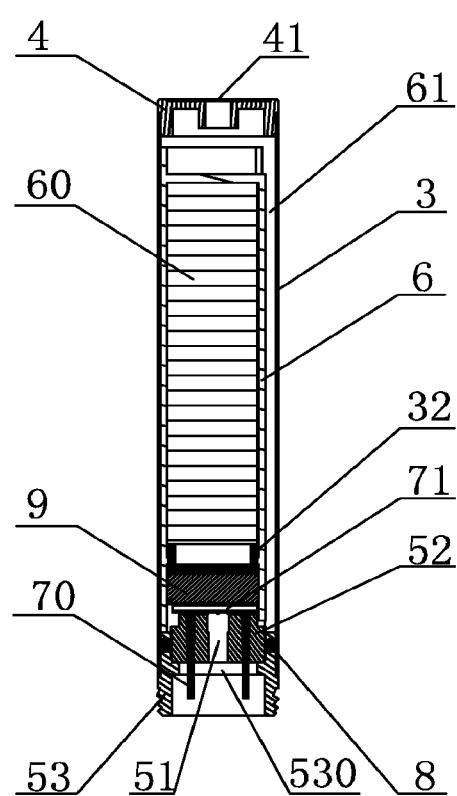

As shown in FIG. 2 and FIG. 4, position-step 31 is provided at the inside of the mouth part of the liquid-container 6, the liquid-container 6 can be plugged by a cap-shaped spacer 32 placed on the position step 31, with liquid-draining apertures 33 provided on the spacer 32. The liquid-guiding device 9 is inserted into the mouth part of the liquid-container 6 behind the spacer 32 and the liquid-draining apertures 33, the spacer 32 thus plugging the mouth part of the liquid-container 6 in advance: the liquid-draining apertures 33 thus slowly guide the liquid 60 in the liquid-container 6 out to the liquid-guiding device 9. In addition, the spacer 32 also limits the assembled depth of the liquid-guiding device 9, so as to avoid the liquid-guiding device 12 being inserted too far into the liquid-container 6 during assembly, and also to prevent the liquid-guiding device 9 from moving towards the liquid-container 6 when the rear closure 5 abuts against the liquid-guiding device 9. The spacer 32 is cap-shaped, which makes it easy for the spacer 32 to be positioned at the inside of the mouth part of the liquid-container 6.

As shown in FIG. 5, the shape of the mouth part of the liquid-container 6 can be of a necked type. The liquid-guiding device 9 then is inserted totally into the mouth part of the liquid-container 6.

Figure 3:
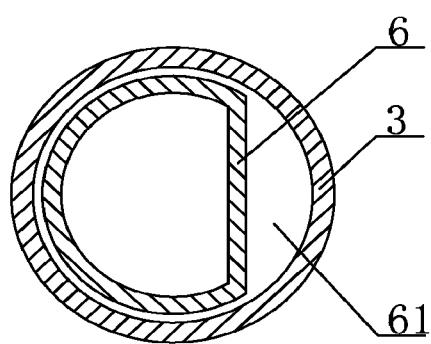

As shown in FIG. 3 and FIG. 4, an airflow-passage 61 is provided between the casing body 3 and the liquid-container 6 to connect the gas-outlet aperture 41 and the gas-inlet aperture 51, which can be either arranged to be around the liquid-container 60 or just one or two side(s) of the liquid-container 6. In this embodiment, one sidewall of the liquid-container 6 is flat, the airflow-passage 61 is formed between the flat-shaped sidewall of the liquid-container 6 and the casing body 3.

As shown in FIG. 2 and FIG. 4, because of the two convex columns 521 are provided on the upper end of the fixing seat for heater 52, the space between the two convex columns 521 and the space around thereof thus form the connection-passage 71 for air-flowing passing through. The air outside enters into the atomizing nozzle 1 at first from the gas-inlet aperture 51, then passes through the connection-passage 71 and gets into the airflow-passage 61, the heated and atomized liquid then flows out along the airflow-passage 61 and the gas-outlet aperture 41.

Another proposal that can be implemented (not shown in Figures) is to arrange a depressed cavity on reserve at the centre of the upper end of the fixing seat for heater 52, which is connected to the gas-inlet aperture 51, the heater 7 is radially-arranged across the top end of the side-wall around the depressed cavity, with through-apertures provided on the side-wall of the depressed cavity, hence, the side-wall around the upper end of the fixing seat for heater 52 then supports the heater 7 against the liquid-guiding device 9 and the heater 7 is also under the liquid-guiding device 9: the depressed cavity then acts as the connection passage 71 (as well as the atomizing cavity), the atomized liquid (gas) then passes through the through-apertures on the side-wall of the depressed cavity and enters into the airflow-passage 61 between the casing body 3 and the liquid-container 6.

As shown in FIG. 2 and FIG. 4, the heater 7 is a kind of part used for heating and atomizing liquid, which is posited between the tops of the convex columns 521 of the fixing seat for heater 52 and is also located in the groove 522, for the convenience of the heater 7 contacting the liquid-guiding device 9 as much as possible. Because the heater 7 itself absorbs the liquid on the liquid-guiding device 9, the liquid-drops spreading in the connection-passage 71 and on the heater 7 can be atomized by making use of the heater 7 and can be carried away by the flowing air to the airflow-passage 61. The heater can be wound from a heat-resistant fibre core 72 to make it easier for the heat-resistant fibre core 72 to absorb the liquid transferred from the liquid-guiding device 9 and the heater 7, and for the heater 7 to atomize the liquid-drops as much as possible.

Another proposal (not shown in the Figures) is to arrange a spreading-spacer at the lower surface of the liquid-guiding device 9, the heater 7 contacts the lower surface of the spreading-spacer, from which the liquid on the liquid-guiding device 9 can be spread more evenly by using the spreading-spacer. The spreading-spacer is a kind of flat-shaped material, with improved spreading characteristics over those of the liquid-guiding device, whilst not necessary better liquid-storage characteristics than the liquid-guiding device. The spreading-spacer can be stuck to the lower surface of the liquid-guiding device 9.

According to the technical proposal described above, the liquid-container 6 can be positioned in the casing body 3, with liquid 60 filled in the liquid-container 6, then the liquid-container 6 is plugged at its mouth part by the liquid-guiding device 9 and the spacer 32, then the rear closure 5, provided with the heater 7, can be assembled into the opening of the rear end of the casing body 3, with the upper end of the rear closure 5 and the heater 7 abutting against the liquid-guiding device 9. The connection-passage 71 is provided between the upper end of the rear closure 5 and the liquid-guiding device 9. Hence, the liquid 60 in the liquid-container 6 spreads to the connection-passage 71, the heater 7 and the heat-resisting fibre core 72 by the liquid-guiding device 9 or the spreading-spacer provided at the lower surface of the liquid-guiding device 9. When the heater 7 is energised, the atomized gas will be drawn out together with the airflow.

The invention claimed is:

1. An atomizing nozzle of an electronic atomizing inhalator, comprising a tubular casing body, provided with a closure wall at an opening of a front end of said casing body, with a gas-outlet aperture on said closure wall; and a rear closure provided at an opening of a rear end of said casing body, with a gas-inlet aperture on said rear closure; a liquid-container and heater being provided in a cavity formed by said casing body, said closure wall and said rear closure; an airflow-passage connecting to the gas-outlet aperture is provided along a radial axis between said casing body and said liquid-container; characterized in that the nozzle further comprises a liquid-guiding device, which closes said liquid-container at an opening of said liquid-container, no liquid-storage medium being arranged in the liquid-container; a connection-passage for connecting the airflow-passage and said gas-inlet aperture is provided between said liquid-guiding device and said rear closure, said heater is provided on a top of said rear closure, contacting a lower surface of said liquid-guiding device, with at least part of said heater located in said connection-passage.

2. An atomizing nozzle of an electronic atomizing inhalator according to claim 1, characterized in that a mouth part of said liquid-container is of a wide-opening type,
    with a position step provided at an inside of said mouth part, a spacer is provided between said position step and said liquid-guiding device, with liquid-draining apertures provided on said spacer.

3. An atomizing nozzle of an electronic atomizing inhalator according to claim 1, characterized in that a spreading-spacer is provided on the lower surface of said liquid-guiding device, said heater contacting the lower surface of said spreading-spacer.

4. An atomizing nozzle of an electronic atomizing inhalator according to claim 1, characterized in that, said heater is wound around a heat-resisting fibre core.

5. An atomizing nozzle of an electronic atomizing inhalator according to claim 1, characterized in that a gas pipe is arranged in said liquid-container, with one end of said gas pipe extending into said liquid-guiding device, and another end of said gas pipe extending to an upper part of said liquid-container.

6. An atomizing nozzle of an electronic atomizing inhalator according to any one of claims 1-5, characterized in that at least part of said liquid-guiding device is inserted into a mouth part of said liquid-container.

7. An atomizing nozzle of an electronic atomizing inhalator according to any one of claims 1-5, characterized in that convex columns are arranged on a top end of said rear closure, with the heater erected across said convex columns, a space around said convex columns then forming said connection-passage.

8. An atomizing nozzle of an electronic atomizing inhalator according to claim 7, characterized in that a semicircular-shaped groove is provided on the top of said convex columns, said heater being erected in said groove.

9. An atomizing nozzle of an electronic atomizing inhalator according to claim 7, characterized in that, a sealing ring is provided between said casing body and the back end of said rear closure.

10. An atomizing nozzle of an electronic atomizing inhalator according to claim 9, characterized in that, said rear closure comprises a fixing seat for said heater and a sealing seat, said fixing seat being provided on said sealing seat, said sealing ring being provided between said sealing seat and said casing body for sealing, said gas-inlet aperture and said convex columns being provided on the top end of said fixing seat for said heater.

11. The atomizing nozzle of claim 1, further comprising the airflow-passage being partially defined by an outer surface of the liquid container.

12. The atomizing nozzle of claim 1, further comprising:
    an outer casing having a circular cross section;
    the liquid container having a truncated circular cross section with a flat portion;
    the outer wall of the liquid container at the flat portion and an adjacent portion of an inner surface of the outer casing defining the airflow-passage.

* * * * *